US010982661B2

(12) United States Patent
Mullins et al.

(10) Patent No.: US 10,982,661 B2
(45) Date of Patent: Apr. 20, 2021

(54) SINGLE MOTOR-GENERATOR TWO-JOINT HARVESTER AND AUGMENTER

(71) Applicant: Bionic Power Inc., Vancouver (CA)

(72) Inventors: Clive Edward Mullins, North Vancouver (CA); Daniel Loren Hepler, Vancouver (CA); Charles David Halliburton, Port Moody (CA)

( * ) Notice: Subject to any disclaimer, the term of this patent is extended or adjusted under 35 U.S.C. 154(b) by 120 days.

(21) Appl. No.: 16/537,920

(22) Filed: Aug. 12, 2019

(65) Prior Publication Data

US 2021/0048007 A1    Feb. 18, 2021

(51) Int. Cl.
| | |
|---|---|
| *F03G 5/06* | (2006.01) |
| *A61F 2/64* | (2006.01) |
| *H02K 7/06* | (2006.01) |
| *H02K 23/50* | (2006.01) |
| *F03G 7/08* | (2006.01) |
| *A61F 2/70* | (2006.01) |

(52) U.S. Cl.
CPC .................. *F03G 5/06* (2013.01); *A61F 2/64* (2013.01); *F03G 7/08* (2013.01); *H02K 7/06* (2013.01); *H02K 23/50* (2013.01); *A61F 2002/708* (2013.01)

(58) Field of Classification Search
CPC ..... F03G 5/06; F03G 5/08; F03G 7/08; A61F 2/64; A61F 2/66; H02K 7/06; H02K 23/50
See application file for complete search history.

(56) References Cited

U.S. PATENT DOCUMENTS

2006/0046908 A1* 3/2006 Rastegar ............ A63B 21/0054
482/91

OTHER PUBLICATIONS

N Lay, Andrea & Hass, Chris & Gregor, Robert. (2006). The effects of sloped surfaces on locomotion: A kinematic and kinetic analysis. Journal of biomechanics. 39. 1621-8. 10.1016/j.jbiomech.2005.05. 005.

Mcintosh, Andrew & T Beatty, Karen & Purcell, Leanne & Vickers, Deborah. (2006). Gait dynamics on an inclined walkway. Journal of biomechanics. 39. 2491-502. 10.1016/j.jbiomech.2005.07.025.

* cited by examiner

*Primary Examiner* — Viet P Nguyen (57) ABSTRACT

A device that attaches to three body segments connected by two joints harvests energy selectively from one of the two joints using a single motor-generator. The device also selectively augments relative body segment motion about one of the two joints. Selection of the harvesting or generating mode depends on the user's preference. When in a particular mode, the device automatically selects which of the two joints to connect to the motor-generator in order to optimize the augmentation or harvesting. Depending on whether the user is on flat terrain, going up an incline or down a decline, the selection of the joint to be connected is different. Use of a single motor-generator and gearbox mounted near the knee reduces metabolic cost compared to the use of two motor-generators and gearboxes.

19 Claims, 5 Drawing Sheets

SINGLE MOTOR-GENERATOR TWO-JOINT HARVESTER AND AUGMENTER

TECHNICAL FIELD

This application relates to augmenting, and harvesting energy from, relative motion of body segments of an animal, particularly a human. In particular, it relates to harvesting energy selectively from one of two joints using a single generator, and also to selectively augmenting motion about one of the joints at a time using the generator as a motor.

BACKGROUND

Energy may be harvested from the movement of body joints of humans and other animals by converting mechanical energy derived from such movement to electrical energy. Activities where body joints move repeatedly, such as walking, jogging, and running, for example, present opportunities to harvest energy from moving body joints over an extended period of time. In some energy harvesting devices and methods, a generator driven by joint motion is coupled to an electrical load.

Muscles may be described as working in a positive mechanical power mode or a negative mechanical power mode. A positive mechanical power mode exists when the product of angular velocity and torque about the associated body joint is positive, i.e. the knee joint is extending and pushing against the external force of gravity on the body away from the ground, or flexing and pulling the foot off the ground against the external force of gravity. A negative mechanical power mode exists when the product of angular velocity and torque about the associated body joint is negative, i.e. the knee joint is extending but resisting that extension, or flexing but resisting that flexion.

Generator torque developed by a harvesting generator always counteracts or opposes motion of a body segment. The generator torque acts against muscles operating on a body segment that is moving in a positive mechanical power mode, thereby increasing the work that must be done by the muscles to move body segment. Harvesting energy from the movement of a body segment when associated muscles are operating in a positive mechanical power mode may be referred to as "non-mutualistic" energy harvesting, since the generator torque associated with such energy harvesting acts against muscles and generally increases the metabolic cost of the associated body segment motion. In contrast, generator torque aids muscles operating on a body segment that is moving in a negative mechanical power mode. Harvesting energy from the movement of a body segment when muscles associated with a body segment are operating in a negative mechanical power mode may be referred to as "mutualistic" energy harvesting, since it aids muscles and generally reduces the metabolic cost of the associated body segment motion.

Some energy harvesters are configured to preferentially harvest energy mutualistically by synchronizing energy harvesting to negative power modes of the body segment. In some such harvesters, control logic achieves such synchronization based on one or more sensed characteristics of the motion of the user to which the body segment belongs. For example, control logic may synchronize energy harvesting to particular gait phase ranges, which it determines based on one or more sensed characteristics of the motion of the user to which body segment belongs.

Energy harvesters that harvest energy from two joints at the same time, however, tend to be inefficient, mainly due to carrying the weight of two generators and two joint selectors.

U.S. Pat. No. 7,652,386 to Donelan et al. relates to an apparatus for harvesting energy from motion of one or more joints. In this apparatus, one or more sensors are used to sense the characteristics associated with the motion of one or more joints, and control circuitry triggers energy harvesting when the conditions during the motion are considered to be mutualistic.

U.S. Pat. No. 10,195,099 to Hepler et al. discloses a device for the intermittent assistance of body segment motion. When the motion of the body segment is cyclical, for example during walking, assistance to the body segment is switched on and off throughout the cycle to correspond to positive and negative power modes respectively. Energy used to assist the body segment may be harvested from prior motion of the body segment, either in prior cycles and/or when the body segment is moving in a negative power mode.

This background is not intended, nor should be construed, to constitute prior art against the present invention.

SUMMARY OF INVENTION

The present invention is a device that harvests energy selectively from one of two joints using exactly one motor-generator, and selectively augments motion about one of the two joints. Selection of the harvesting or generating mode depends on the user's preference or can be set automatically. When in a particular mode, the device automatically selects which of the two joints to connect to the motor-generator in order to optimize the augmentation or harvesting. Depending on whether the user is on flat terrain, going up an incline or down a decline, the selection of the joint to be connected can be different.

An advantage of an embodiment of the device is that only a single motor-generator is required, which saves weight and reduces metabolic cost compared to the use of two motor-generators. A further advantage of an embodiment of the device is that exactly one joint selector is needed instead of the two that would be required if there were two motor-generators. Another advantage of an embodiment of the device is that the motor-generator and the joint selector are located close to the knee, which reduces metabolic cost compared to having them or equivalent components mounted near the foot.

Disclosed herein is a device for harvesting energy from and augmenting motion of a first joint and a second joint of an animal body, wherein the first joint connects a first and a second body segment of the animal and the second joint connects the second and a third body segment of the animal, the device comprising: a first brace which attaches to the first body segment, a second brace which attaches to the second body segment, and a third brace which attaches to the third body segment; a motor-generator that is switchable between a harvesting mode and an augmentation mode; and a joint selector that has a first position and a second position, wherein: the first position mechanically links the motor-generator to the first brace and the second brace so that relative rotation between the first brace and the second brace correlates with rotation of the motor-generator; and the second position mechanically links the motor-generator to the second brace and the third brace so that relative rotation between the second brace and the third brace correlates with rotation of the motor-generator.

Also disclosed is a method for harvesting energy from and augmenting motion of a first joint and a second joint of an animal body, wherein the first joint connects a first and a second body segment of the animal and the second joint connects the second and a third body segment of the animal, the method comprising: attaching a first brace to the first body segment, a second brace to the second body segment, and a third brace to the third body segment; detecting, by one or more sensors, a grade of a terrain that the animal is traversing; setting a motor-generator to an augmentation mode or a harvesting mode; controlling, by a control module in response to the detected grade, the motor-generator and a joint selector that has a first position and a second position, wherein: the first position mechanically links the motor-generator to the first brace and the second brace so that relative rotation between the first brace and the second brace correlates with rotation of the motor-generator; and the second position mechanically links the motor-generator to the second brace and the third brace so that relative rotation between the second brace and the third brace correlates with rotation of the motor-generator.

BRIEF DESCRIPTION OF DRAWINGS

The following drawings illustrate embodiments of the invention and should not be construed as restricting the scope of the invention in any way.

DESCRIPTION

A. Glossary

The term "augmentation" is used to refer to the assistance to a user of the device. In some cases, the added torque is in the same direction of motion of the body segment; in other cases the torque opposes the direction of motion of the body segment.

The term "body segment" may refer to a part of a body, such as a thigh, lower leg or foot for example. It may also refer to one or more muscles of the body segment, such as a hamstring and a quadriceps. Further, a body segment may also comprise multiple, constituent body segments, depending on how they are defined. Most muscle groups span across two joints. For instance, the hamstring (i.e. the biceps femoris and semitendinosus) spans from pelvis to tibia, and the gastrocnemius spans from condyles of the femur to the calcaneus (heel bone) across both the knee and ankle joints. As a consequence, contraction of a muscle may affect multiple skeletal body segments.

The term "device" when used without qualification includes, but is not limited to, the collection of mechanical and electronic components of a single motor-generator, two joint harvester and augmenter.

The term "dorsiflexion" refers to bending the foot upwards.

The term "harvesting" is used when the user is being assisted in the negative power mode, i.e. when the motor-generator is generating electricity and, as a consequence, opposing the direction of motion of the body segment. Harvesting may also occur in the positive power mode, in which the motion is also opposed, but at a higher metabolic cost.

The term "negative power mode" refers to a situation where, for example, the knee torque and angular velocity have opposite signs.

The term "plantarflexion" refers to bending the foot downwards.

The term "sensor" includes, but is not limited to, a device or module that detects events or changes in its environment and sends the information to other electronic devices, or has an output that is detected by other devices.

The term "torque" refers to a moment of force that produces rotation or torsion, or opposes rotation or torsion.

B. Exemplary Embodiments

Figure 1:
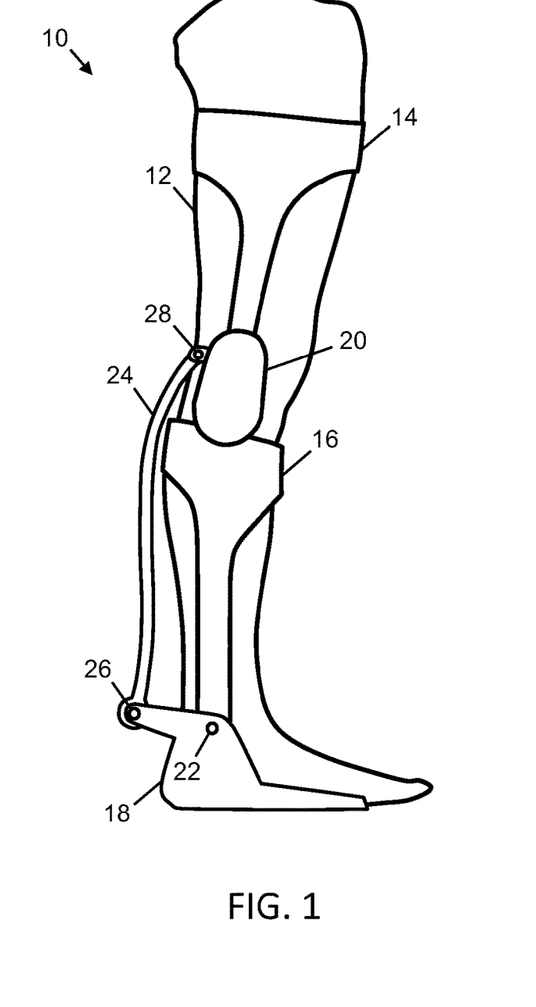
FIG. 1 is a schematic representation of a single motor-generator, two joint harvester and augmenter, according to an embodiment of the present invention.

Referring to FIG. 1, an overview of the main physical components of the device are shown. A single motor-generator, two-joint harvester and augmenter device 10 is attached to a human leg 12. The device 10 has a thigh brace 14, a shin brace 16 (or lower leg brace) and a foot brace 18. A housing 20 forming part of the device 10 is rigidly mounted on the shin brace 16 and can move relative to the thigh brace 14. The housing 20 includes a joint selector and a motor-generator. The foot brace 18 is pivoted to the shin brace 16 via pivot 22, and is connected via arm 24 and pivots 26 and 28 to the joint selector in the housing 20.

Figure 2:
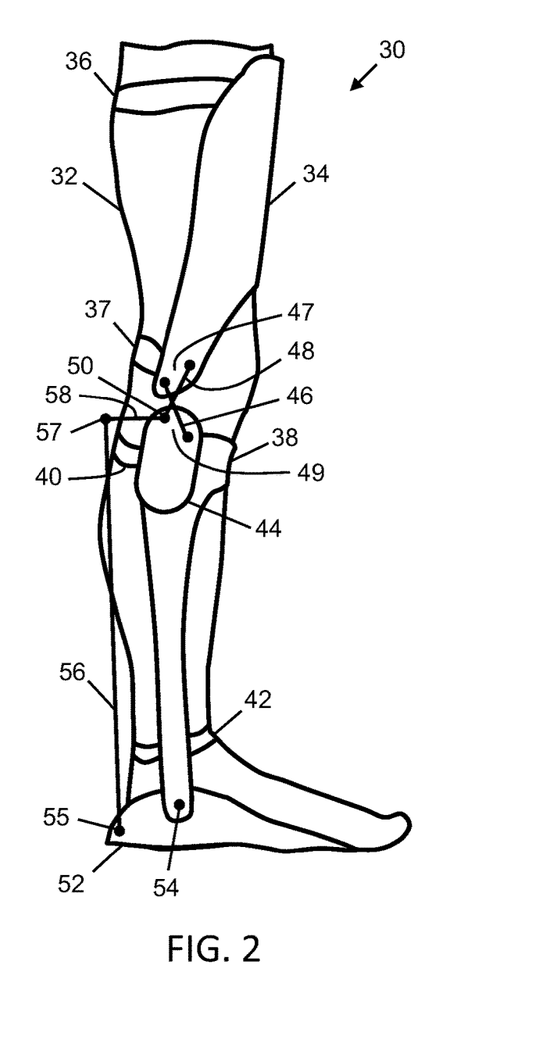
FIG. 2 is a schematic representation of a single motor-generator, two joint harvester and augmenter, showing linkages between various components, according to an embodiment of the present invention.

Referring to FIG. 2, details of various of the linkages are shown. A single motor-generator, two-joint harvester and augmenter device 30 is shown attached to a human leg 32. The device 30 has a thigh brace 34, which is fastened to the thigh by straps 36 and 37. A shin brace 38 (or lower leg brace) is attached to the lower leg by straps 40 and 42.

A housing 44 forming part of the device 30 is rigidly mounted on the shin brace 38 and can move relative to the thigh brace 34. The housing 44 includes a joint selector and a motor-generator. The housing 44 is connected to the thigh brace 34 via a steady-ratio four-bar genuflective linkage, for example as described in U.S. Pat. No. 10,075,046. The four-bar linkage is made up of linkages 46, 48, the lower portion 47 of the thigh brace 34 and the upper portion 49 of the housing 44. The four-bar linkage allows relative motion between the thigh brace 34 and the shin brace 38 that mimics the relative motion between the thigh and the lower leg as the knee bends.

The foot brace 52 is pivoted to the shin brace 38 via pivot 54, and is connected via arm 56 and pivots 55 and 57 to linkage 58.

Linkage 48 and linkage 58 rotate back and forth about axis 50 as the user wearing the device 30 walks or runs or otherwise traverses a terrain. The joint selector inside the housing 20 connects one of the linkages 48, 58 at a time to the single motor-generator inside the housing. The motor-generator can then therefore augment or harvest from either the knee or the ankle, but not both at the same time. The joint selector can also disconnect both the linkages 48, 58 from the motor-generator to allow freer movement of the knee and ankle joints.

The location of the housing 44 in which the joint selector is present is immediately below the knee, at the top end of the shin brace, for low metabolic cost and also for the ability to directly drive the two linkages 48, 58. The additional metabolic cost of carrying the housing 44 just below the knee is not significantly higher than if the housing were positioned just above the knee, as in single joint energy harvesters that harvest energy from the knee. If the housing were at the ankle joint, a considerably greater metabolic cost would be incurred by the user.

The arm 56 is, for example, carbon fiber or fiberglass, which has a higher efficiency than cable, and enables bidirectional torque with a single transmission. A carbon fiber arm can provide high plantarflexion torque when in tension and a lower, but sufficient dorsiflexion torque when in compression.

Figure 3:
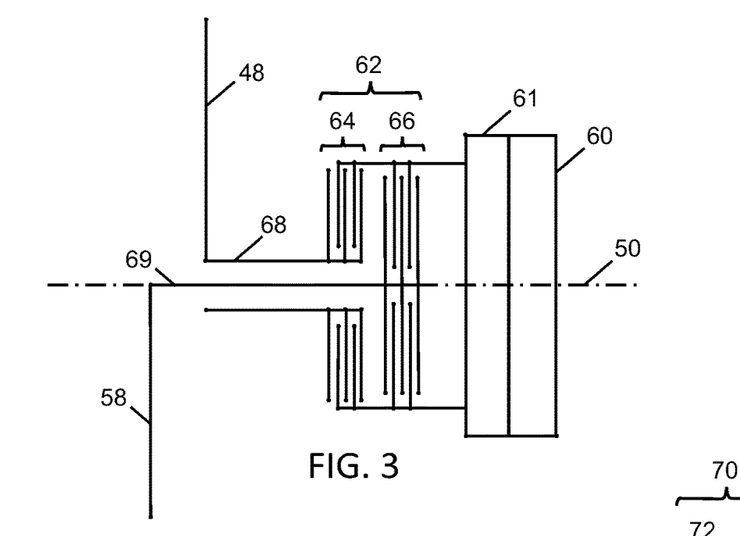
FIG. 3 is a schematic cross-sectional representation of a simple joint selector for the single motor-generator, two joint harvester and augmenter, according to an embodiment of the present invention.

Referring to FIG. 3, the principle of operation is shown. Exactly one motor-generator 60 that rotates about axis 50 is connected to exactly one, gearbox 61, which is in turn connected to clutch assembly 62 that has clutches 64, 66. The clutch assembly 62 is a mechanical joint selector, which selects the body joint that is connected to the motor-generator. Linkage 48, which rotates back and forth about axis 50 when the knee bends is connected by hollow shaft 68 to one side of the clutch 64, the other side of the clutch 64 being connected via the gearbox 61 to the motor-generator 60. Linkage 58, which rotates back and forth about axis 50 when the ankle bends is connected by shaft 69 to one side of the clutch 66, the other side of the clutch 66 being connected via the gearbox 61 to the motor-generator 60.

In operation, only one of the clutches 64, 66 is activated at a time, or neither of them are activated. When clutch 64 is activated, rotation of the linkage 48 either drives the motor-generator 60 or is driven by the motor-generator. When clutch 66 is activated, rotation of the linkage 58 either drives the motor-generator 60 or is driven by the motor-generator. As such, the rotation of each linkage 48, 58, and therefore the rotation of the corresponding joint, is correlated with the rotation of the motor-generator when connected.

Figure 4:
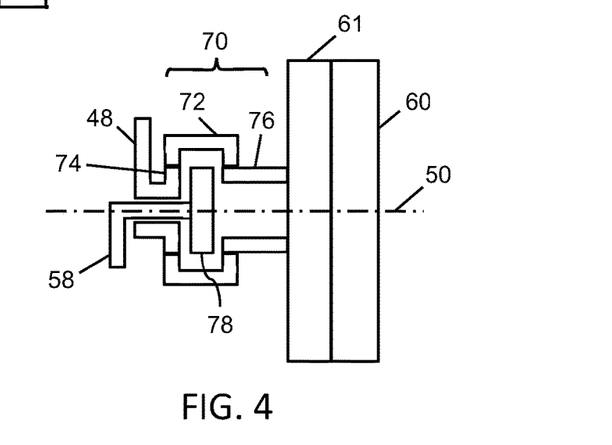
FIG. 4 is a schematic cross-sectional representation of a sliding spline joint selector for the single motor-generator, two joint harvester and augmenter, with the knee linkage engaged, according to an embodiment of the present invention.

FIG. 4 shows another type of joint selector 70, which operates using a sliding spline 72 (or selector collar). Linkage 48, which rotates back and forth about axis 50 when the knee bends, is connected to spline 74, which follows the rotation of the linkage 48. The sliding spline 72 is shown in a position that connects the spline 74 to the spline 76, which in turn is connected via the gearbox 61 to the motor-generator 60. As the linkage 48 rotates, the motor-generator 60 rotates. Rotation of the linkage 48 either drives the motor-generator 60 or is driven by the motor-generator when the sliding spline 72 is in this position.

Linkage 58, which rotates back and forth about axis 50 when the ankle bends, is connected to spline 78, which follows the rotation of the linkage 58. The sliding spline 72 is in a position that does not connect spline 78 to spline 76. Therefore, the linkage 58 rotates independently of the rotation of the motor-generator 60.

The sliding spline 72 may be, for example, a miniature version of an automotive synchronizer ring. Speed matching is not necessary, however, as transitions can be made under algorithmic control at zero speed crossing.

Figure 5:
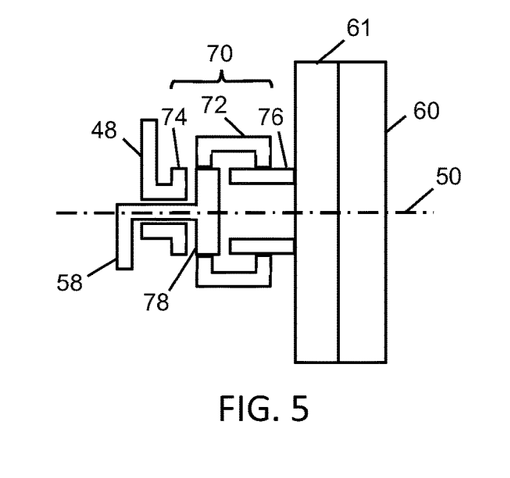
FIG. 5 is a schematic representation of the sliding spline joint selector with the ankle linkage engaged, according to an embodiment of the present invention.

FIG. 5 shows the sliding spline joint selector 70 with the sliding spline 72 in another position. In this position, the sliding spline 72 connects spline 78 to the spline 76. Therefore, as the linkage 58 rotates, the motor-generator 60 rotates via the gearbox 61. Rotation of the linkage 58 either drives the motor-generator 60 or is driven by the motor-generator when the sliding spline 72 is in this position.

Linkage 48 is not connected by the sliding spline 72 to spline 76, because the sliding spline 72 is in a position that does not connect the spline 74 to spline 76. Therefore, the linkage 48 rotates independently of the rotation of the motor-generator 50.

Figure 6:
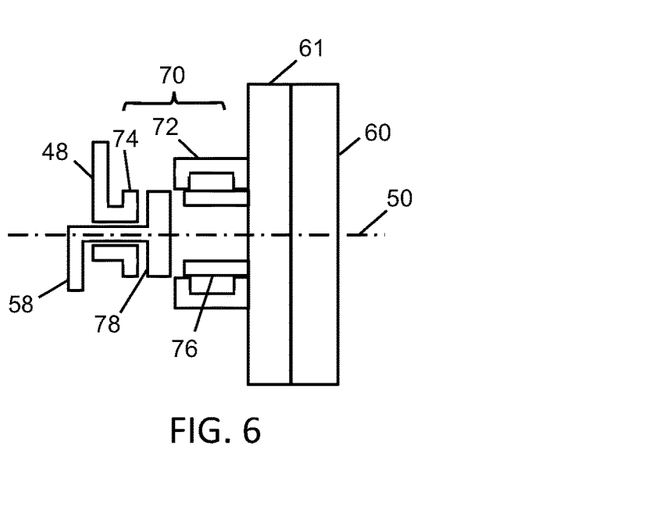
FIG. 6 is a schematic representation of the sliding spline joint selector with neither linkage engaged, according to an embodiment of the present invention.

FIG. 6 shows the sliding spline joint selector 70 with the sliding spline 72 in a third or neutral position. In this position, the sliding spline 72 does not connect either of the splines 74, 78 to the spline 76. Linkages 48, 58 are therefore not connected to the motor-generator 60 and so the linkages 48, 58 rotate independently of the rotation of the motor-generator 60.

In other embodiments, there may not be a neutral position of the joint selector, and the joint that remains connected to the motor-generator is effectively disconnected electrically, by not drawing current from, or providing current to, the motor-generator.

C. Control

In broad terms, harvesting energy from the knee is good when the user is going downhill. Also, in broad terms, augmenting the knee is good when the user is going downhill, and augmenting the ankle is good when the user is going uphill. More specifically, TABLE 1 gives the joints that are targeted depending on whether the device 30 is in an augmenting mode or a harvesting mode, and whether the user is walking up an incline, on the level or down a decline. Selection of the harvesting or generating mode depends on the user's preference or is set automatically. When in a particular mode, the device automatically selects the joint, if any, to connect to the motor-generator in order to optimize the augmentation or harvesting. Depending on whether the user is on flat terrain, going up an incline or down a decline, the selection of the joint to be connected can be different. Note that, when the device is in augmentation mode and the user is going down a decline, the augmentation to the knee joint is the provision of opposing torque, by which the motor-generator generates electricity.

TABLE 1

| Mode | Grade | Connected Joint |
| --- | --- | --- |
| Augment | Incline | Ankle |
| Augment | Level | Ankle |
| Augment | Decline | Knee |
| Harvest | Incline | Knee/neither |

TABLE 1-continued

| Mode | Grade | Connected Joint |
|---|---|---|
| Harvest | Level | Knee |
| Harvest | Decline | Knee |

Figure 7:
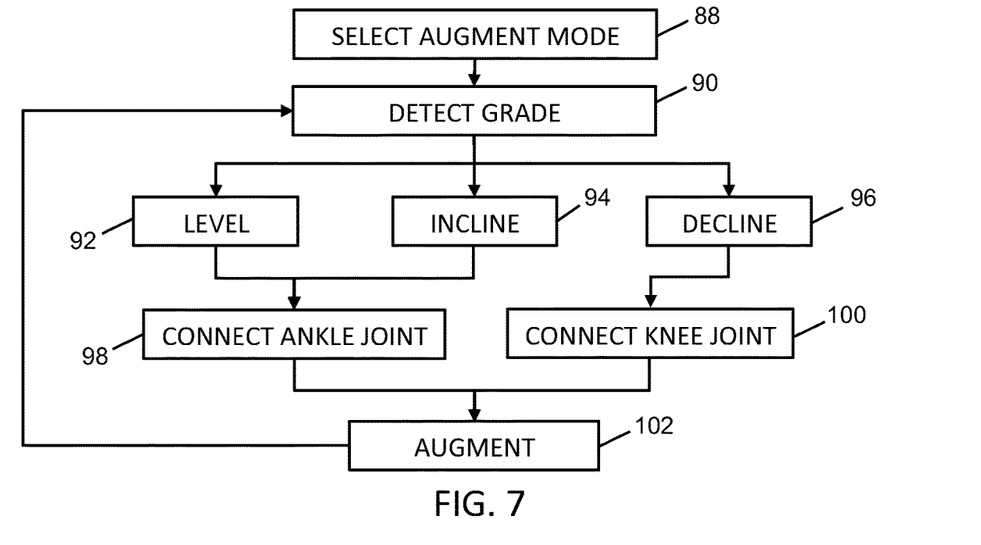
FIG. 7 is a flowchart for augmenting with the single motor-generator, two joint harvester and augmenter, according to an embodiment of the present invention.

FIG. 7 shows a process that the device 30 undertakes when the user desires to use the device for augmentation. In step 88, the user selects the augmentation mode. In other embodiments, the device 30 may automatically detect that the user is becoming tired and as a result, automatically enter the augmentation mode. The device 30, in some embodiments, may also automatically enter the augmentation mode depending on other factors, such as the difficulty of the terrain and the distance to the destination.

In step 90, the device 30 detects the grade of the terrain that the user is traversing. There are multiple methods by which this can be achieved. For example, the determination of the grade can be model-based, using one or more of knee, ankle and hip angle and angular velocity detected by one or more sensors. This model-based approach compares the real-time sensor data and/or past stride(s) sensor data against models of what particular grades (i.e. incline/level/decline) look like in the model. Another method is in real-time, based on inertial measurement unit data (e.g. from an accelerometer and gyroscope) that is put through a Kalman filter or similar type of filter. There are some computationally less expensive filters than Kalman filters that have similar properties. Foot pressure sensors may also be used in some embodiments to improve the robustness of detection of the stance phase. In other embodiments, a combination of any of the above may be used.

In step 92, the device 30 determines that the grade is level, and as a result it operates the joint selector to connect the ankle joint to the motor-generator in step 98. This also has the effect of disconnecting the knee joint from the motor-generator. When the ankle joint has been connected to the motor-generator, the device 30 then begins to augment motion of the ankle joint in step 102.

In step 94, the device 30 determines that the grade is an incline, and as a result it operates the joint selector to connect the ankle joint to the motor-generator in step 98. As above, this also has the effect of disconnecting the knee joint from the motor-generator. When the ankle joint has been connected to the motor-generator, the device 30 then begins to augment motion of the ankle joint in step 102.

In step 96, the device 30 determines that the grade is a decline, and as a result it operates the joint selector to connect the knee joint to the motor-generator in step 100. This also has the effect of disconnecting the ankle joint from the motor-generator. When the knee joint has been connected to the motor-generator, the device 30 then begins to augment motion of the knee joint in step 102.

Augmentation of either the knee joint or the ankle joint is usually intermittent, in that augmentation only occurs during portions of the gait. Normally, augmentation involves the motor-generator operating as a motor, to provide extra torque to the joint in the direction is it moving. However, in some cases, augmentation involves using the motor-generator as a generator, providing resistance to the motion of the joint. For example, when going downhill or down stairs, resistance is provided to the knee joint as it flexes, to counteract the force of gravity on the user.

The process then reverts to step 90, such that the grade of the terrain is repeatedly detected. If the grade changes as the user progresses across the terrain, then the joint that is connected to the motor-generator is changed accordingly.

Figure 8:
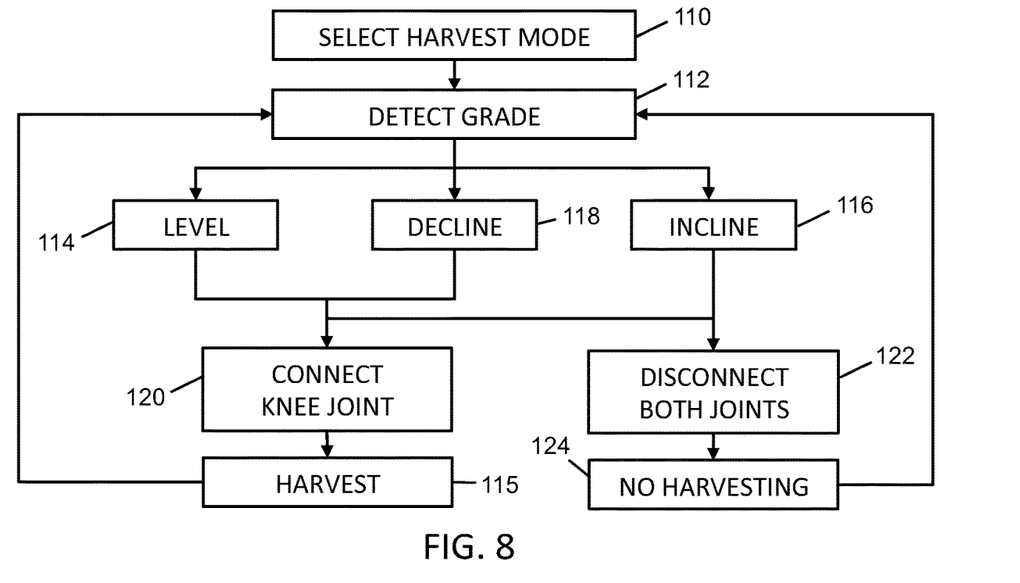
FIG. 8 is a flowchart for harvesting with the single motor-generator, two joint harvester and augmenter, according to an embodiment of the present invention.

FIG. 8 shows a process that the device 30 undertakes when the user desires to use the device for harvesting. In step 110, the user selects the harvesting mode. In other embodiments, the device 30 may automatically enter the harvesting mode, for example if a battery that is connected to the device needs to be charged. The device 30, in some embodiments, may also automatically enter the harvesting mode depending on other factors, such as the ease of the terrain, speed of the user and the expected time needed to reach the destination.

In step 112, the device 30 detects the grade of the terrain that the user is traversing. In step 114, the device 30 determines that the grade is level, and as a result it operates the joint selector to connect the knee joint to the motor-generator in step 120. This also has the effect of disconnecting the ankle joint from the motor-generator. When the knee joint has been connected to the motor-generator, the device 30 then begins to harvest energy from the motion of the knee joint in step 115.

In step 116, the device 30 determines that the grade is an incline, and as a result it operates the joint selector to either connect the knee joint to the motor-generator in step 120 or disconnect both the knee joint and the ankle joint from the motor-generator in step 122. When the knee joint has been connected to the motor-generator in step 120, the device 30 then begins to harvest energy from the motion of the knee joint in step 115. However, when both the knee and ankle joints are disconnected in step 122, the device proceeds to step 124 in which no harvesting occurs from the knee and ankle joints. The decision whether or not to harvest when the terrain becomes an incline is made dependent on a user setting or automatically, depending on the steepness of the incline, the speed at which the user is climbing, the time to a destination, the need to generate electricity or any other relevant parameter.

The process then reverts to step 112, such that the grade of the terrain is repeatedly detected. If the grade changes as the user progresses across the terrain, then the decision as to whether to harvest or not is changed accordingly.

In step 118, the device 30 determines that the grade is a decline, and as a result it operates the joint selector to connect the knee joint to the motor-generator in step 120. This also has the effect of disconnecting the ankle joint from the motor-generator. When the knee joint has been connected to the motor-generator, the device 30 then begins to harvest energy from the motion of the knee joint in step 115.

The process then reverts to step 112, such that the grade of the terrain is repeatedly detected. If the grade changes as the user progresses across the terrain, then the decision as to whether to harvest or not is changed accordingly.

Harvesting from the knee joint (or the ankle joint where implemented) is usually intermittent, in that harvesting only occurs during portions of the gait. Harvesting involves the motor-generator operating as a generator, providing torque that opposes the direction in which the joint is moving.

The motion of body segments rotating about a joint can be described as a succession of negative and positive power modes within each cycle of motion. In one embodiment the device is configured to take advantage of the negative power modes in order to generate and store energy, without harvesting from the positive power modes. A negative power mode exists when the angular velocity of the joint between the segments and the torque are in opposite directions. In one example case of a negative power mode, the muscles of the leg act as a brake at various moments during the gait. In other embodiments, harvesting occurs in both negative and positive power modes. As such, the harvesting may be mutualistic, or both mutualistic and non-mutualistic, depending on the embodiment and/or the configuration of the device.

Figure 9:
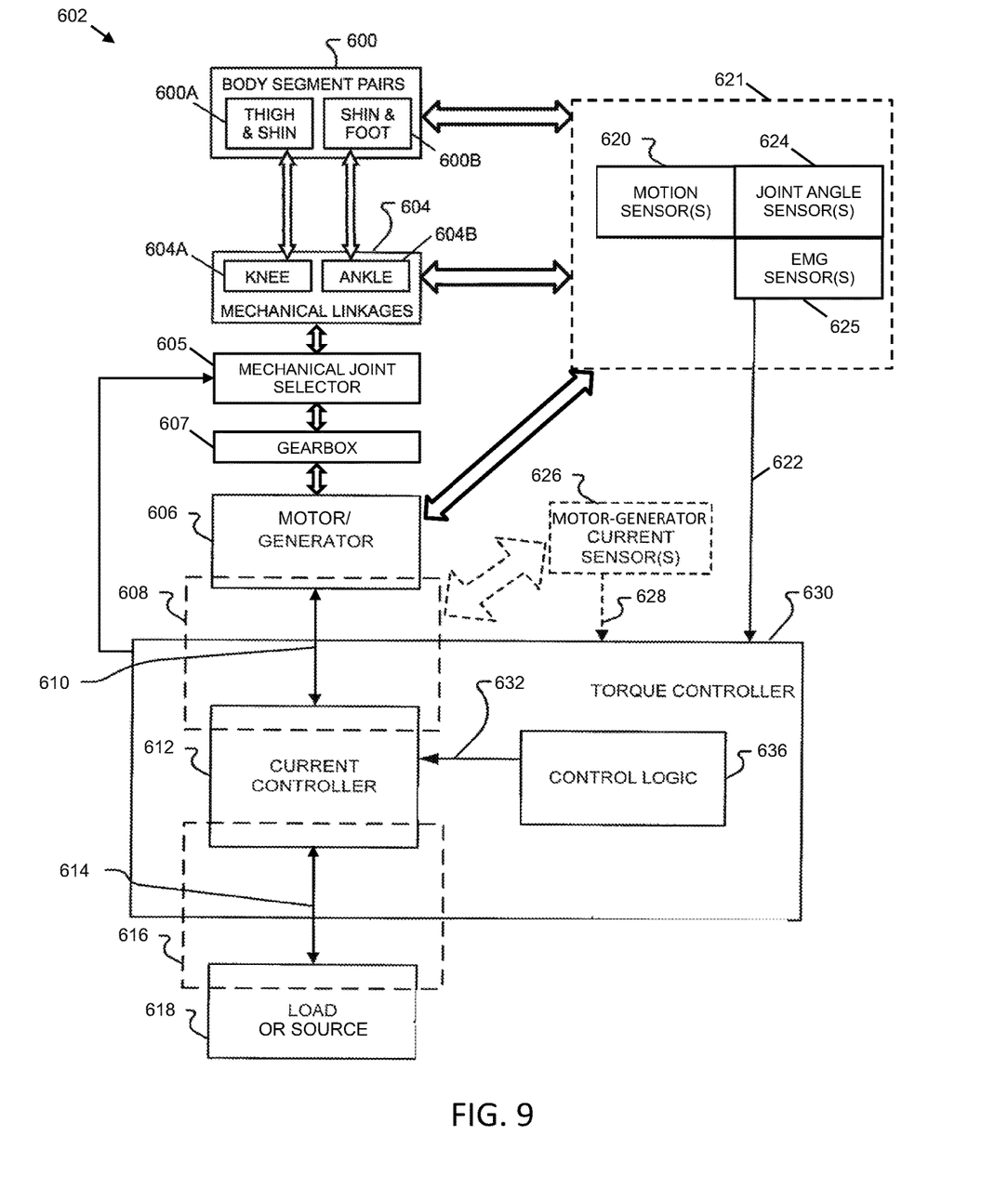
FIG. 9 is a schematic diagram of a single motor-generator, two joint harvester and augmenter, according to an embodiment of the present invention.

Referring to FIG. 9, components of a single motor-generator, two joint harvester and augmenter device 602 are shown. A motor-generator 606 is coupled by a gearbox 607 and mechanical joint selector 605 to the mechanical linkages 604 and the corresponding pairs of body segments 600 of the user. Specifically, in a first position, the joint selector 605 connects the motor-generator 606 via the knee's mechanical linkage 604A to the thigh and shin body segment pair 600A. In a second position, the joint selector 605 connects the motor-generator 606 via the ankle's mechanical linkage 604B to the shin and foot body segment pair 600B.

Motion of one or more of the body segments 600 is analyzed by sensors 621, including, for example motion sensor(s) 620, joint angle sensor(s) 624 (e.g. knee angle sensor and ankle angle sensor) and one or more EMG sensors 625. Mechanical linkages 604 are also analyzed by sensors 621, e.g. the motion sensor(s) 620 and joint angle sensors 624. Joint angle sensors on the mechanical linkage 604 and joint angle sensors that measure the actual angle of the joint may provide different angles depending on the amount of slack between the body segments 600 and the mechanical linkage.

Motor-generator 606 is also analyzed by the sensor(s) 621, e.g. the motion sensor(s) 620. Data gathered by the sensors 621 is transmitted to the torque controller 630 via connection 622. The motor-generator 606 is electrically connected to the torque controller 630, which controls the motor torque developed by motor-generator when operating as a motor in an augmentation mode. Torque controller 630 is electrically connected via connection 614 to an electrical load 618 (e.g. rechargeable battery) and is configured to control the supply of current from motor-generator 606 to load when the motor-generator is operating in harvesting mode. In particular embodiments, torque controller 630 comprises a current controller 612, which controls the current supplied to the motor-generator 606 and (since this current is at least approximately proportional to the motor torque) thereby controls the motor torque developed by the motor-generator 606.

In the illustrated embodiment, the torque controller 630 also comprises control logic 636. The motor-generator current sensor circuit 626 provides an electrical connection between motor-generator 606 and current controller 612. The motor-generator current sensor circuit 626 comprises an input/output connection 610 between the motor-generator 606 and the current controller 612. Connection 610 may operate as an output from the current controller 612 and an input to the motor-generator 606 when the system 602 is operating in augmentation mode. Conversely, connection 610 may operate as an output from the motor-generator 606 and an input to the current controller 612 when the system 602 is operating in energy harvesting mode. Motor-generator current sensor circuit 626 may also comprise other circuit components not expressly shown, e.g. rectifying components, amplifiers, signal conditioning circuits, drivers, inverters, timers and/or the like.

Torque controller 630 may optionally receive a feedback signal 628 reflective of generator current drawn from motor-generator 606, or of drive current supplied to the motor-generator. In some embodiments, motor-generator current feedback signal 628 may be provided by one or more current sensor(s) 626. In other embodiments, motor-generator circuit 608 may be designed to provide motor-generator current feedback signal 628 directly, i.e. without the need for separate current sensor(s) 626. In some embodiments, current sensor(s) 626 may detect, and/or motor-generator current feedback signal 628 may be reflective of, the current drawn from motor-generator 606 after rectification, i.e. generator current feedback signal 628 may be reflective of a DC generator current level.

The torque controller 630 also controls operation of the mechanical joint selector 605. For example, the mechanical joint selector 605 is operated by activating a solenoid within the joint selector.

In the illustrated embodiment, current controller 612 controls the motor-generator current based at least in part on a torque control signal 632 (which may also be referred to as a torque reference signal 632). For example, current controller 612 may attempt to cause the motor current of the motor-generator 606 to track torque control signal 632. In the illustrated embodiment, torque control signal 632 is generated by control logic 636 and may be indicative of a magnitude of the desired motor torque to be developed in motor-generator 606 and/or a magnitude of the desired motor current to be supplied to motor-generator 606. Control logic 636 may comprise one or more suitably configured central processing units (CPU), one or more microprocessors, one or more microcontrollers, one or more field-programmable gate arrays (FPGA), application-specific integrated circuits (ASIC), logic circuits, combinations thereof or any other suitable processing unit(s) comprising hardware and/or firmware and/or software capable of functioning as described herein. In some embodiments, control logic 636 may be implemented in the analog domain by a suitably designed analog control circuit.

A load and source circuit 616 provides the electrical connection between current controller 612 and load or source 618. Load and source circuit 616 comprises a connection 614 from current controller 612, which is electrically connected to load or source 618. Load and source circuit 616 may also comprise other circuit components not expressly shown, e.g. rectifying circuits, amplifiers, signal conditioning circuits, capacitors, super capacitors, rechargeable batteries and/or the like. Depending on the embodiment, load and source circuit 616 may be completely outside of the torque controller 630.

Figure 10:
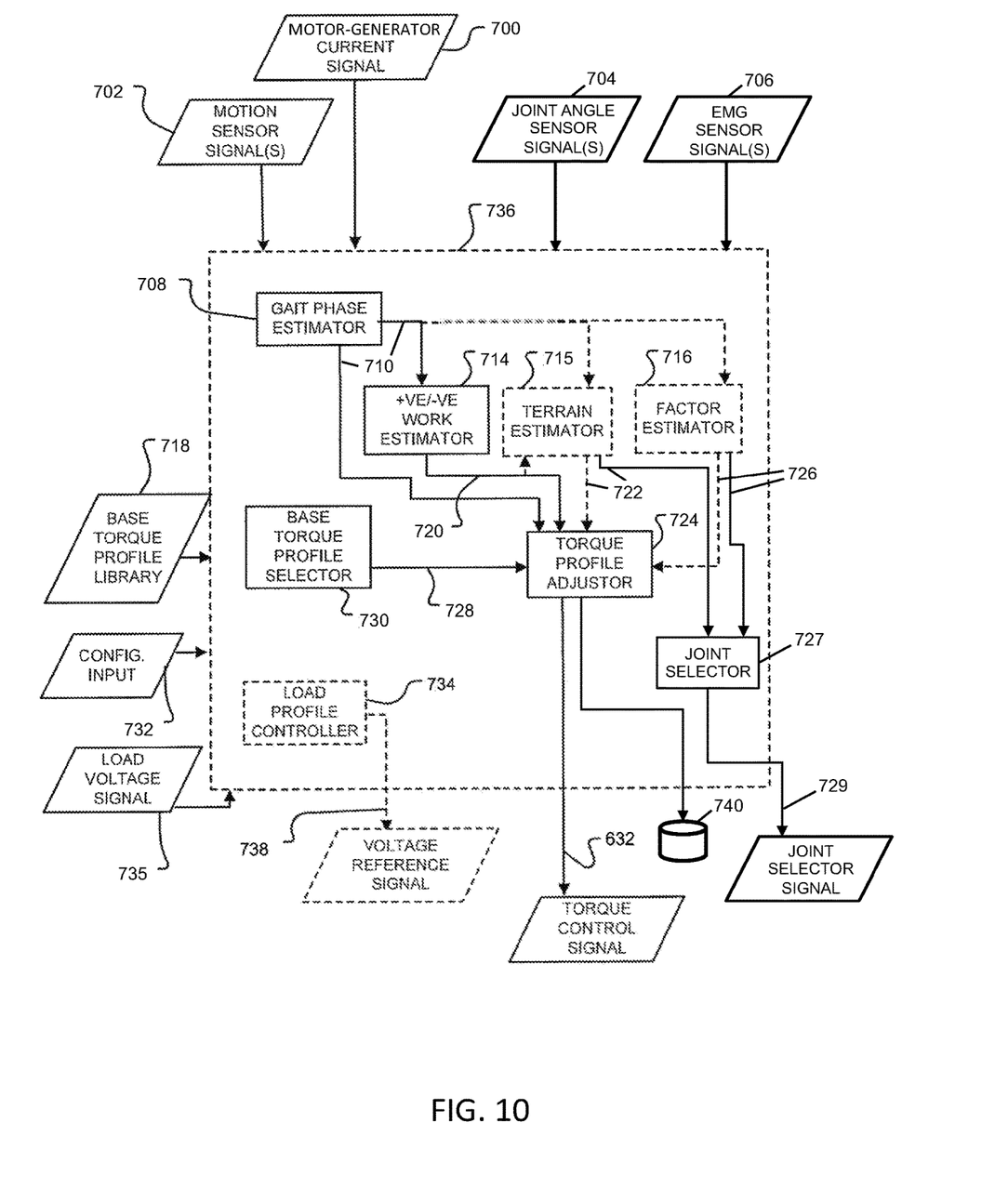
FIG. 10 schematically depicts control logic according to a particular embodiment of the single motor-generator, two joint harvester and augmenter.

Referring to FIG. 10, control logic 736 is shown according to a particular embodiment. Control logic 736 may be used as, or as a part of, control logic 636 of device 602 (FIG. 9) and may be used to determine torque control signal 632 discussed above. In the illustrated embodiment, control logic 736 receives a number of inputs, which include: motion sensor signal(s) 702 (e.g. from motion sensor(s) 620) indicative of one or more aspects of the motion of body segments 600; EMG sensor signal(s) 706 (e.g. from EMG sensor(s) 625) indicative of one or more aspects of the muscle activity of body segment 600; motor-generator current signal 700 (e.g. from motor-generator current sensor(s) 626) indicative of the current output of or current input to motor-generator 606; joint angle sensor signal(s) 704 (e.g. from joint angle sensor(s) 624) indicative of the current joint angular position; a base torque profile library input 718; and a configuration input 732.

In the illustrated embodiment, where an ankle or knee joint connects body segments 600 and energy is applied thereto, control logic 736 comprises a gait phase estimator 708. Gait phase estimator 708 generates a gait phase estimate signal 710 indicative of the current phase of the gait of body segments 600. Gait phase estimator 708 may use information from motion sensor signal(s) 702 and/or EMG sensor signals 706 to generate its gait phase estimate signal 710. Motion sensor signal(s) 702 may comprise the three phase voltage output signals from motor-generator 606 which may be used to estimate the angular velocity of the motor-generator and the corresponding relative angular velocity of body segments 600. In some embodiments, gait phase estimator 708 may also make use of other inputs (e.g. motor-generator current feedback signal 700 or other inputs from other sensors) to generate its gait phase estimate signal 710. In some embodiments, gait phase estimator 708 may additionally or alternatively estimate whether the current gait phase is within one of the particular portions of a gait cycle which spans a range of gait phases, e.g. whether the knee joint is in swing flexion, swing extension, stance/ collision flexion or stance extension. In one particular embodiment, gait phase estimator 708 may determine the transitions between gait phase portions and output information in gait phase estimate signal 710 indicating that a transition has occurred between gait portions.

Positive/negative work estimator 714 may make use of a variety of information to ascertain whether the motion of body segments 600 is in a positive or negative mechanical power mode. By way of non-limiting examples, such information may include gait phase estimate signal 710, motion sensor signal(s) 702, EMG sensor signal(s) 706, and/or motor-generator current feedback signal 700. In one particular non-limiting example, positive/negative work estimator 714 may use gait phase estimator signal 710 to determine the time of transitions between portions of a user's gait cycle.

Control logic 736 may also comprise an optional terrain estimator 715 which may be used in embodiments where body segments 600 include a portion of the user's body associated with locomotion (e.g. the user's knee or ankle joint). Terrain estimator may attempt to ascertain whether the motion of a body segment 600 is being influenced by the terrain being traversed by the user. The output of terrain estimator 715 may be provided as output signal 722, which may include, for example, an indication of the angular grade of the terrain being traversed by the user. Terrain estimator 715 may make use of a variety of information to generate terrain estimate signal 722. By way of a non-limiting example, such information may include gait phase estimate signal 710, positive/negative power mode signal 720, motion sensor signal(s) 702, EMG sensor signals 706 and/or motor-generator current feedback signal 700 which may be analyzed over a past number of gait cycles, for example. Detecting terrain and slope types may be desirable to optimize body-segment motion assistance and/or energy harvesting during specific phases or portions of the gait, or to increase user comfort during more intense locomotion over difficult terrain.

Terrain represents just one of many types of factors which may have an impact on repetitive motion associated with a body segment 600, the desirability of providing assistive power to the body segment at any given time and how much energy should be provided to the body segment at any given time.

The output 722 from the terrain estimator 715 along with user intent, which is either determined automatically (via factor estimator 716) or via input from the user (via configuration input 732), are passed to the joint selector module 727, which generates control signals 729 for activation of the sliding spline 72 or clutches 64, 66 to select the joint to be connected to the motor-generator 60. The joint selector signal 729 is an output of the control logic 736. The activation of the clutch or sliding spline is achieved with a solenoid or by energizing electro-static clutch plates, for example.

Factor estimator 716 may make use of a variety of information to generate factor estimator output signal 726. Factors which may be estimated may be defined as every event or those which may have an impact on repetitive motion associated with the body segments, such as for example gait cadence, speed of movement, user, user-specific gait parameters, user size, load carried by the user, location of carried load or locomotion type. By way of non-limiting examples, information used to generate factor estimator output may include gait phase estimate signal 710, positive/negative power mode signal 720, motion sensor signal(s) 702 and/or motor-generator current feedback signal 700, and/or one or more other appropriate signals.

Control logic 736 may comprise a base torque profile selector 730, which serves the purpose of selecting a base torque profile 728 from a library 718 of base torque profiles. Base torque profile library 718 may comprise a library of base torque profiles for different types of repetitive motions, different types of gaits and different types of terrain. The selection of a particular base torque profile 728 by base torque profile selector 730 may be based, in part, in configuration input 732. The configuration input 732 may comprise user-configurable input information about the pre-categorization of the user, prior or intended use of the device 602, experimentally determined information about the use of other similar devices, calibration information of the device and its use, device constant information and/or the like.

Control logic 736 may comprise a torque profile adjuster 724, which adjusts the base torque profile (in an initial iteration) and/or a current torque profile (in subsequent iterations) in response to a variety of input information to provide (as output) torque control signal 632. Torque control signal 632 may be provided to current controller 612 as discussed above. Torque profile adjuster 724 may receive input information which may include, without limitation: base torque profile 728, gait phase estimator output 710, positive/negative work estimator output 720, terrain estimator output 722, factor estimator output 726, configuration input 732, motion sensor signal(s) 702 and/or motor-generator current signal 700. While not explicitly shown, torque profile adjustor 724 may maintain a current torque profile which includes the most recent updates to the torque profile to be tracked. The current torque profile may be saved in accessible memory or the like and may provide the basis for torque control signal 632 output from torque profile adjuster 724.

Non-limiting examples of types of adjustments that may be made to torque profiles by torque profile adjustor 724 include, without limitation:

scaling and/or offsetting the entire torque profile in the torque domain (e.g. to compensate for user size);

scaling and/or offsetting of the entire torque profile in the time domain or in a "percentage of gait cycle" domain (e.g. to compensate for gait cadence);

scaling and/or offsetting of portions of the torque profile (e.g. one or more portions of the torque profile, one or more sub-parts of a portion in a torque profile and/or one or more transition periods between portions in a torque profile) in the torque domain (e.g. to more efficiently provide assistive power to a body segment throughout a gait cycle);

scaling and/or offsetting of portions of the torque profile (e.g. one or more portions of the torque profile, one or more sub-parts of a portion in a torque profile and/or one or more transition periods between portions in a torque profile) in the time domain or in a "percentage of gait cycle" domain (e.g. to compensate for different host gait profiles or to ensure host safety);

scaling and/or offsetting of the rate(s) of transitions (e.g. torque profile slopes) between different torque levels in a torque profile;

offsetting the location(s) in the time domain or in a "percentage of gait cycle" domain of changes in a torque profile; and/or scaling of the entire torque profile to a constant level.

The torque profile adjuster 724, in some embodiments, stores the adjusted torque profiles and parameters representative of the behaviour of the device 602 in the database 740.

Control logic 736 comprises an optional load profile controller 734, which outputs a voltage control signal 738. Load profile controller 734 may use information from load voltage feedback signal 735 to generate voltage control signal 738. In some embodiments, load profile controller 734 may also make use of configuration input 732 and/or other inputs to generate voltage control signal 738. By way of non-limiting example, configuration input 732 may include parameters of load and/or parameters of generator 606.

D. Variations

While the best presently contemplated mode of carrying out the subject matter disclosed and claimed herein has been presented, other embodiments are possible.

In other embodiments, the single motor-generator may comprise multiple motor-generators in a single motor-generator unit, i.e. a unit that is connectable by a single joint selector to either the knee joint, the ankle joint or neither, but not both the knee joint and the ankle joint at the same time.

Joint selectors may, in other embodiments, be made more compact than shown above, so that the device protrudes less from the outer side of the user's leg. For example, the joint selector and the motor-generator may be configured to lie in the same plane rather than side by side. Different mechanical configurations of the joint selector are possible in other embodiments, provided that the joint selector serves to connect only one joint at a time to the motor-generator. In other embodiments, further gears may be used to connect the linkages 48, 58 to the motor-generator, for example to change the drive ratio or to position the various components of the device differently. The motor-generator 60, in some embodiments, includes further gears, which may be selectable to change the drive ratio.

In some embodiments the motor-generator includes multiple windings which are individually, dynamically and automatically selectable depending on the amount of harvesting or amount of augmentation required.

While the description has been made largely in relation to a human knee and ankle joint, the device may be adapted to other pairs of human joints, and to animal joints.

Structural modifications may be added to the device in order to increase the surface area of one or more of the thigh brace, the shin brace or the foot brace, for the purpose of minimizing and spreading the impact of the pressure on the user's body. Moreover, this increased surface area reduces the movement of the device relative to the leg.

The system may include an accelerometer to detect motion of body segments. Segway™-style gyroscopes may also be used in some embodiments, such as vibrating structure gyroscopes or inclinometers. Dead-reckoning techniques may be used in some embodiments to determine the position within a particular cycle of a gait, to calculate a location of the user, or to determine a gradient of the terrain that the user is traversing.

The foregoing embodiments and aspects thereof are described and illustrated in conjunction with systems, tools and methods that are intended to be exemplary and illustrative, and not limiting in scope.

Throughout the description, specific details have been set forth in order to provide a more thorough understanding of the invention. However, the invention may be practiced without these particulars. In other instances, well known elements have not been shown or described in detail and repetitions of steps and features have been omitted to avoid unnecessarily obscuring the invention. Accordingly, the specification is to be regarded in an illustrative, rather than a restrictive, sense.

It will be clear to one having skill in the art that further variations to the specific details disclosed herein can be made, resulting in other embodiments that are within the scope of the invention disclosed. All configurations described herein are examples only and actual ones depend on the specific embodiment. Accordingly, the scope of the invention is to be construed in accordance with the substance defined by the following claims.

The invention claimed is:

1. A device for harvesting energy from and augmenting motion of a first joint and a second joint of an animal body, wherein the first joint connects a first and a second body segment of the animal and the second joint connects the second and a third body segment of the animal, the device comprising:
   a first brace which attaches to the first body segment, a second brace which attaches to the second body segment, and a third brace which attaches to the third body segment;
   a motor-generator that is switchable between a harvesting mode and an augmentation mode; and
   a joint selector that has a first position and a second position, wherein:
      the first position mechanically links the motor-generator to the first brace and the second brace so that relative rotation between the first brace and the second brace correlates with rotation of the motor-generator; and
      the second position mechanically links the motor-generator to the second brace and the third brace so that relative rotation between the second brace and the third brace correlates with rotation of the motor-generator.

2. The device of claim 1, wherein the animal is a human.

3. The device of claim 1, wherein:
   the first joint is a knee joint, the second joint is an ankle joint, the first body segment is a thigh, the second body segment is a shin and the third body segment is a foot, all of a single leg of a human body;
   the first brace is a thigh brace;
   the second brace is a shin brace; and
   the third brace is a foot brace.

4. The device of claim 3, comprising a fiberglass or carbon fiber arm that connects the foot brace to the joint selector.

5. The device of claim 3, comprising a housing that is mounted on the shin brace, wherein the joint selector and the motor-generator are inside the housing.

6. The device of claim 5 wherein the housing is mounted at a top end of the shin brace.

7. The device of claim 1, comprising: one or more sensors configured to detect a grade of a terrain on which the device is being used; a control module configured to control the motor-generator and the joint selector using the detected grade.

8. The device of claim 7, wherein:
when the motor-generator is in the augmentation mode and the grade is a decline, the control module selects the first position of the joint selector; and
when the motor-generator is in the augmentation mode and the grade is level or an incline, the control module selects the second position of the joint selector.

9. The device of claim 7, wherein:
the joint selector has a third position that does not link the motor-generator to the thigh brace and the shin brace, and does not link the motor-generator to the thigh brace and the shin brace;
when the motor-generator is in the harvesting mode and the grade is level or a decline, the control module selects the first position of the joint selector; and
when the motor-generator is in the harvesting mode and the grade is an inline, the control module selects the first position or third position of the joint selector.

10. The device of claim 1, wherein the joint selector comprises:
a first clutch that is activated in the first position of the joint selector; and
a second clutch that is activated in the second position of the joint selector.

11. The device of claim 1, wherein the joint selector comprises a sliding spline that moves from a first location in the first position of the joint selector to a second location in the second position of the joint selector.

12. The device of claim 11, wherein:
the joint selector has a third position that does not link the motor-generator to the thigh brace and the shin brace, and does not link the motor-generator to the shin brace and the foot brace; and
the sliding spline is at a third location in the third position of the joint selector.

13. The device of claim 1, wherein, when the device is in the augmentation mode, the motor-generator operates intermittently as a generator and intermittently as a motor.

14. The device of claim 1, wherein, when the device is in the harvesting mode, the motor-generator operates intermittently as a generator.

15. A method for harvesting energy from and augmenting motion of a first joint and a second joint of an animal body, wherein the first joint connects a first and a second body segment of the animal and the second joint connects the second and a third body segment of the animal, the method comprising:
attaching a first brace to the first body segment, a second brace to the second body segment, and a third brace to the third body segment;
detecting, by one or more sensors, a grade of a terrain that the animal is traversing;
setting a motor-generator to an augmentation mode or a harvesting mode;
controlling, by a control module in response to the detected grade, the motor-generator and a joint selector that has a first position and a second position, wherein:
the first position mechanically links the motor-generator to the first brace and the second brace so that relative rotation between the first brace and the second brace correlates with rotation of the motor-generator; and
the second position mechanically links the motor-generator to the second brace and the third brace so that relative rotation between the second brace and the third brace correlates with rotation of the motor-generator.

16. The method of claim 15, wherein the animal is a human.

17. The method of claim 15, wherein: when the motor-generator is in the augmentation mode and the grade is a decline, the method comprises selecting the first position of the joint selector; and when the motor-generator is in the augmentation mode and the grade is level or an incline, the method comprises selecting the second position of the joint selector.

18. The method of claim 15, wherein: the joint selector has a third position that does not link the motor-generator to the thigh brace and the shin brace, and does not link the motor-generator to the thigh brace and the shin brace; when the motor-generator is in the harvesting mode and the grade is level or a decline, the method comprises selecting the first position of the joint selector; and when the motor-generator is in the harvesting mode and the grade is an inline, the method comprises selecting the first position or third position of the joint selector.

19. The method of claim 15, wherein: the first joint is a knee joint, the second joint is an ankle joint, the first body segment is a thigh, the second body segment is a shin and the third body segment is a foot, all of a single leg of a human body; the first brace is a thigh brace; the second brace is a shin brace; and the third brace is a foot brace.

* * * * *